US008318215B1

(12) United States Patent
Ryngler-Lewensztain et al.

(10) Patent No.: US 8,318,215 B1
(45) Date of Patent: Nov. 27, 2012

(54) COMPOSITION AND METHOD OF PREPARING A TOMATO-BASED TOPICAL FORMULATION FOR ENHANCED HEALING OF BURNS, ULTRAVIOLET AND RADIATION ERYTHEMA

(75) Inventors: Miriam Ryngler-Lewensztain, Beverly Hills, CA (US); Gabriel Green, Sherman Oaks, CA (US)

(73) Assignee: Miriam Ryngler-Lewensztain, Beverly Hills, CA (US)

( * ) Notice: Subject to any disclaimer, the term of this patent is extended or adjusted under 35 U.S.C. 154(b) by 0 days.

(21) Appl. No.: 12/799,239

(22) Filed: Apr. 21, 2010

(51) Int. Cl.
*A61K 36/00* (2006.01)
*A61K 36/81* (2006.01)
(52) U.S. Cl. ........................ 424/725; 424/764
(58) Field of Classification Search ................ None
See application file for complete search history.

(56) References Cited

U.S. PATENT DOCUMENTS

| | | | |
|---|---|---|---|
| 6,623,769 B1 | 9/2003 | Lorant et al. | |
| 6,780,444 B1 | 8/2004 | Reza | |
| 6,953,574 B2 | 10/2005 | Sobol et al. | |
| 7,048,943 B2 | 5/2006 | Barenholz et al. | |
| 7,189,419 B2 | 3/2007 | Mahalingam et al. | |
| 2002/0183248 A1 | 12/2002 | Oldham et al. | |
| 2005/0266018 A1 | 12/2005 | Boreyko et al. | |
| 2006/0013782 A1 | 1/2006 | Mahalingam et al. | |
| 2006/0105059 A1 | 5/2006 | McArthur | |
| 2007/0031367 A1* | 2/2007 | Brown et al. | 424/74 |
| 2007/0148286 A1* | 6/2007 | Jani et al. | 426/5 |
| 2007/0202197 A1 | 8/2007 | McArthur | |
| 2007/0286916 A1 | 12/2007 | Bengmark | |

FOREIGN PATENT DOCUMENTS

| | | | |
|---|---|---|---|
| CN | 101248861 A | * | 8/2008 |
| GB | 1122796 | | 8/1968 |
| JP | 2000229827 A | * | 8/2000 |
| JP | 2000229828 | | 8/2000 |
| JP | 2000229828 A | * | 8/2000 |
| JP | 2008239545 A | * | 10/2008 |

OTHER PUBLICATIONS

McMillan, Leatherman et al., "Cellular Effects of Long Wavelength UV Light in Mammalian Cells." J. Pharm Pharmacol 60(8):969-76, 2008.
Fitzpatrick TB. "The Validity and Practicality of Sun Reaction Types . I . through VI. Arch Dermatol" (1988) 124-869-871.
Fitzpatrick, TB. (1986) "Ultraviolet-induced pigmentary changes: Benefits and Hazards." Curr Probl Derm 15:25-38.
Stahl, W. "Carotenoids and flavonoids contribute to nutritional protection against skin damage . . . " Mol Biotechnol. 37(1):26-30, 2007.
Stahl, W. Lycopene-rich products and dietary photoprotection. Photochem Photobiol. Sci. 5(2): 238-42, 2006.
Aust, O., "Supplementation with tomato-based products increases lycopene . . . " Int. J. Vitam Nutr Res. 75(1): 54-60, 2005.
Stahl, W. "Tomato Paste protects against ultraviolet light-induced erythema in humans". J. Nutr. 131(5): 1449-51, 2001.
Cesarini, JP, "Immediate effects of UV radiation on the skin: modification by an antioxidant complex" Photodermatol Photoimmunol Photomed. 19(4) :182-9, 2003.
Heinrich, U. "Supplementation with beta-carotene of similar amount of mixed carotenoids . . . " J. Nutr. 133(1) :98-101, 2003.
Greul, AK, "Photoprotection of UV-Irradiated human skin", Skin Parmacol Appl. Skin Physiol. 15(5) :307-15, 2002.
Stahl, W. "Carotenoids and protection against solar UV radiation." Skin Pharmacol Appl Skin Physiol. 15(2): 291-6,2002.
Sies, H, Non-nutritive bioactive constituents of plants: lycopene, lutein and zeaxanthin. Int J. Vitam Nutr Res. 73(2):95-100,2003.
Dinkova-Kostova, AT. "Phytochemicals as protectors against ultraviolet radiation", Planta Med. 74(13):1548-59, 2008.
Weiss, JF, "Protection against ionizing radiation by antioxidant nutrietns." Toxicology 189(1-2): 1-20, 2003.
Maenthaison, R. "The efficacy of aloe vera used for burn wound healing: A systematic review." Burns 33(6):713-8, 2007.
Vogler, BK, "Aloe vera: a systematic review of its clinical effectiveness." Br J Gen Pract. 49)447): 823-8. 1999.
Richardson, J. (Aloe vera for preventing radiation-induced skin reactions. Clin Oncol (R Coll Radiol). 17(6):478-84, 2005.
Kaufman, T. "Aloe vera gel hindered wound healing of experimental second-degree burns". J Burn Care Rehabil. 9(2):156-9, 1998.
Reuter, J. "Investigation of the anti-inflammatory potential of Aloe vera gel." Skin Pharmacol Physiol. 21(2):106-10, 2008.
Bostrom, A. "Potent corticosteroid cream significantly reduces acute radiation dermatitis". Radiother Oncol. 59(3):257-65, 2001.
Mnich, CD. "Green Tea Extract Reduces Induction of p53 and apoptosis in UVB-irradiated human skin . . . " Exp Dermatol. 18(1): 69-77, 2009.
Lincz, LF, "Thrombin generation as a predictor or radiotherapy induced skin erythema." Radiother Oncol. 90(1):136-40, 2009.
Carver, GW. "How to Gro the Tomato and 115 Ways to Prepare it for the Table." Tuskegee Institute Press, Buleetin 36, 1936.

* cited by examiner

*Primary Examiner* — Qiuwen Mi
(74) *Attorney, Agent, or Firm* — Thomas I. Rozsa

(57) ABSTRACT

The present invention is a topical treatment. which can be in the form of cream, ointment, spray or other topically administered composition, which is used to enhance healing of burns, ultraviolet and radiation erythema. The treatment not only reduces pain and inflammation, prevents blistering, and maintains flexibility of the skin, but also accelerates the normal healing process.

1 Claim, No Drawings

COMPOSITION AND METHOD OF PREPARING A TOMATO-BASED TOPICAL FORMULATION FOR ENHANCED HEALING OF BURNS, ULTRAVIOLET AND RADIATION ERYTHEMA

BACKGROUND OF THE INVENTION

1. Field of the Invention

The present invention relates to the field of topical preparations in forms such as ointment or spray which accelerate the healing of thermal injury, ultraviolet injury or radiation induced burns to the skin of humans, other mammals and other living creatures.

2. Description of the Prior Art

Skin is the primary protective barrier for humans. Healthy skin is a major factor in overall health. Skin can be injured by mechanical disruption (e.g., cuts and scrapes), by internal mechanisms (e.g., infiltrative disease) or by absorption of energy (e.g., heat, ultraviolet, and ionizing radiation). This study focuses on the acceleration of the healing of skin injuries caused by the absorption of various forms of energy: heat, ultraviolet and ionizing radiation.

Heat causes thermal skin injury. Burns are classified as first, second or third degree by the extent of the injury.

Degree Characteristics

1 Affects only the outer layer of the skin. Symptoms: pain, redness, and swelling. (sunburn, thermal injury)
2 Affects both the outer and underlying layer of skin. Symptoms: pain, redness, swelling, and blistering.
3 Extends into deeper tissues. Symptoms: White or blackened, charred skin that may be numb.

First- and second-degree burns are a common first aid problem. They cause pain, redness and swelling; progressing to blistering in many cases. The discomfort during healing is the primary morbidity of thermal injury. Extensive wounds and third degree burns require expert medical intervention. Burn injury is usually independent of skin type.

Ultraviolet light causes sunburn. Not all skin is equally resistant to ultraviolet injury. A common skin phenotype classification is based on the likelihood of the skin to burn or tan.

| Type | Skin Color | Characteristics |
| --- | --- | --- |
| 1 | White | Always burns, never tan |
| 2 | White | Usually burns, tans less than average |
| 3 | White | Sometimes mild burn, tans more than average |
| 4 | White | Rarely burns, tans more than average |
| 5 | Brown | Rarely burns, tans profusely |
| 6 | Black | Never burns, deeply pigmented |

White skin is at greater risk of ultraviolet light injury. Ultraviolet radiation injury causes pain, redness and swelling, i.e. inflammation. The discomfort during healing is the primary morbidity of sunburn.

Sunscreens, protective clothing and limiting exposure are the traditional methods to protect skin from ultraviolet induced injury. Dietary intake of carotenoids or other photoprotective compounds can increase protection of skin against injury by ultraviolet or ionizing radiation.

Skin exposed to the high energy photons in ionizing radiation develops burns not unlike severe sunburn. Radiation-induced erythema is a comorbidity of radiation treatment in oncology.

Topical therapy is the first line therapy for minor burns, whether heat, ultraviolet or radiation induced. Anesthetics in the topical formulations mask the pain of burns while the skin heals itself.

Humans have used plants and plant extracts as topical medications to treat various conditions from the dawn of remembered history. The use of mosses, muds and plants are well known in the "fable and folklore" pharmacopeia. George Washington Carver recognized the medicinal value of the tomato in the early 20th century. The classical treatment for burns is the plant or an extract of *Aloe vera*. A review of individual studies and meta analyses reveals few positive results or little objective evidence for any positive effect, and notably, some negative effects of *Aloe vera* extracts on various burn injuries. Other plant derived polyphenols and extracts have been evaluated topically with mixed results. Synthetic medications, such as topical corticosteroids are effective in acute radiation dermatitis although there may be substantial side effects.

The following published articles have addressed the subject matter of treatment of burns and various remedies that are known or have been considered in the prior art.

1. McMillan T J, Leatherman E, Ridley A, Shorrocks J, Tobi S E, Whiteside J R Cellular effects of long wavelength UV light (UVA) in mammalian cells. J Pharm Pharmacol 60(8): 969-76, 2008.
2. Fitzpatrick T B. The validity and practicality of sun reaction types I through VI. Arch Dermatol (1988) 124: 869-871.
3. Fitzpatrick T B. (1986) Ultraviolet-induced pigmentary changes: Benefits and hazards. Curr Probl Derm 15:25-38.
4. Stahl W, Sies H. Carotenoids and flavonoids contribute to nutritional protection against skin damage from sunlight. Mol Biotechnol. 37(1):26-30, 2007.
5. Stahl W, Heinrich U, Aust O, Tronnier H, Sies H. Lycopene-rich products and dietary photoprotection Photochem Photobiol Sci. 5(2):238-42, 2006.
6. Aust O, Stahl W, Sies H, Tronnier H, Heinrich U. Supplementation with tomato-based products increases lycopene, phytofluene, and phytoene levels in human serum and protects against UV-light-induced erythema. Int J Vitam Nutr Res. 75(1):54-60, 2005.
7. Stahl W, Heinrich U, Wiseman S, Eichler O, Sies H, Tronnier H. Dietary tomato paste protects against ultraviolet light-induced erythema in humans. J. Nutr. 131(5):1449-51, 2001.
8. Césarini J P, Michel L, Maurette J M, Adhoute H, Bejot M. Immediate effects of UV radiation on the skin: modification by an antioxidant complex containing carotenoids. Photodermatol Photoimmunol Photomed. 19(4):182-9, 2003.
9. Heinrich U, Gärtner C, Wiebusch M, Eichler O, Sies H, Tronnier H, Stahl W. Supplementation with beta-carotene or a similar amount of mixed carotenoids protects humans from UV-induced erythema. J Nutr. 133(1):98-101, 2003.
10. Greul A K, Grundmann J U, Heinrich F, Pfitzner I, Bernhardt J, Ambach A, Biesaiski H K, Goilnick H. Photoprotection of UV-irradiated human skin: an antioxidative combination of vitamins E and C, carotenoids, selenium and proanthocyanidins. Skin Pharmacol Appl Skin Physiol. 15(5):307-15, 2002.
11. Stahl W, Sies H. Carotenoids and protection against solar UV radiation. Skin Pharmacol Appl Skin Physiol. 15(5): 291-6, 2002.
12. Sies H, Stahl W. Non-nutritive bioactive constituents of plants: lycopene, lutein and zeaxanthin. Int J Vitam Nutr Res. 73(2):95-100, 2003.

13. Dinkova-Kostova A T. Phytochemicals as protectors against ultraviolet radiation: versatility of effects and mechanisms. Planta Med. 74(13):1548-59, 2008.
14. Weiss J F, Landauer M R Protection against ionizing radiation by antioxidant nutrients and phytochemicals. Toxicology 189(1-2):1-20, 2003.
15. Maenthaisong R, Chaiyakunapruk N, Niruntraporn S, Kongkaew C. The efficacy of aloe vera used for burn wound healing: a systematic review. Burns 33(6):713-8, 2007.
16. Vogler B K, Ernst E. *Aloe vera*: a systematic review of its clinical effectiveness. Br J Gen Pract. 49(447):823-8, 1999.
17. Richardson J, Smith J E, McIntyre M, Thomas R, Pilkington K. *Aloe vera* for preventing radiation-induced skin reactions: a systematic literature review. Clin Oncol (R Coll Radiol). 17(6):478-84, 2005.
18. Kaufman T, Kalderon N, Ullmann Y, Berger J. *Aloe vera* gel hindered wound healing of experimental second-degree burns: a quantitative controlled study. J Burn Care Rehabil. 9(2): 156-9, 1998.
19. Reuter J, Jocher A, Stump J, Grossjohann B, Franke G, Schempp C M. Investigation of the anti-inflammatory potential of *Aloe vera* gel (97.5%) in the ultraviolet erythema test. Skin Pharmacol Physiol. 21(2):106-10, 2008.
20. Boström A, Lindman H, Swartling C, Berne B, Bergh J. Potent corticosteroid cream (mometasone furoate) significantly reduces acute radiation dermatitis: results from a double-blind, randomized study. Radiother Oncol. 59(3): 257-65, 2001.
21. Mnich C D, Hoek K S, Virkki L V, Farkas A, Dudli C, Laine E, Urosevic M, Dummer R. Green tea extract reduces induction of p53 and apoptosis in UVB-irradiated human skin independent of transcriptional controls. Exp Dermatol. 18(1):69-77, 2009.
22. Lincz L F, Gupta S A, Wratten C R, Kilmurray J, Nash S, Seldon VI, O'Brien P C, Bell K J, Denham J W. Thrombin generation as a predictor of radiotherapy induced skin erythema. Radiother Oncol. 90(1):136-40, 2009.
23. Carver, G W How to Grow the Tomato and 115 Ways to Prepare It For the Table. Tuskegee Institute Press, Bulletin 36, 1936.

The following 13 patents and published patent applications are also relevant prior art:
1. United States Published Patent Application No. 2002/0183248 to Michael J. Oldham et al. on Dec. 5, 2002 for "Method Of Using Lectins For Prevention And Treatment Of Skin Diseases And Disorders" (hereafter the "Oldham Published Patent Application");
2. U.S. Pat. No. 6,623,769 issued to Raluca Lorant et al. on Sep. 23, 2003 for "Administration Of Lycopene For Combating Skin/Mucous Membrane Damage" (hereafter the "Lorant Patent");
3. U.S. Pat. No. 6,780,444 issued to Alma Reza on Aug. 24, 2004 for "Method Of Making Cosmetic, Pharmaceutical, And Dermatological Compositions And Compositions Made According To The Method" (hereafter the "Reza Patent");
4. U.S. Pat. No. 6,953,574 issued to Constantin Vladimirovich Sobol et al. and assigned to Technology Commercialization, Inc. on Oct. 11, 2005 for "Method For Producing A Fermented Hydrolyzed Medium Containing Microorganisms" (hereafter the "Sobol Patent");
5. United States Published Patent Application No. 2005/0266018 to Benson K. Boreyko et al. on Dec. 1, 2005 for "Nutraceutical Compositions With Mangosteen" (hereafter the "Boreyko Published Patent Application");
6. United States Published Patent Application No. 2006/0013782 to Harish Mahalingam et al. on Jan. 19, 2006 for "Use Of Active Extracts To Improve The Appearance Of Skin. Lips, Hair And/Or Nails" (hereafter the "Mahalingam Published Patent Application");
7. United States Published Patent Application No. 2006/0105059 to Thomas James McArthur on May 18, 2006 for "Fruit And/Or Vegetable Derived Composition" (hereafter the "'0105059 McArthur Published Patent Application");
8. U.S. Pat. No. 7,048,943 issued to Yeckezkel Barenholz et al. and assigned to Yissum Research Development Company of the Hebrew University of Jerusalem on May 23, 2006 for "Carotenoid-Loaded Liposomes" (hereafter the "Barenholz Patent");
9. U.S. Pat. No. 7,189,419 issued to Harish Mahalingam et al. and assigned to Avon Products, Inc. on Mar. 13, 2007 for "Use Of Active Extracts To Lighten Skin, Lips, Hair, And/Or Nails" (hereafter the "Mahalingam Patent");
10. United States Published Patent Application No. 2007/0202197 to Thomas James McArthur on Aug. 30, 2007 for "Pawpaw And/Or Peach Derived Composition" (hereafter the "'0202197 McArthur Published Patent Application");
11. United States Published Patent Application No. 2007/0286916 to Stig Bengmark on Dec. 13, 2007 for "Synbiotic Use" (hereafter the "Bengmark Published Patent Application");
12. European Patent No. 1,122,796 issued to Gustave Giradiere on Aug. 7, 1968 for "Composition For Making A Coating On Human Tissue" (hereafter the "Giradiere European Patent");
13. Patent Abstract of Japan No. 2000229828 issued to Uehara Shizuka et al. and assigned to Kose Corp on Aug. 22, 2000 for "Skin Bleaching Lotion" (hereafter the "Shizuka Patent Abstract of Japan").

The Oldham Published Patent Application discloses a method of using lecithin for prevention and treatment of skin diseases and disorders. The inventor believed that lecithin could be administered in a variety of forms for the delivery to dermal surfaces, either topically or subcutaneously.

The Lorant Patent deals with treating cosmetic effects of aging by administering topically compositions which include lycopene. The patent teaches "A method for treating an individual having cutaneous signs of aging caused by expression of proteases in the extracellular matrix comprising administering to said individual an amount of lycopene effective to substantially inhibit the expression of said proteases in the extracellular matrix of said individual."

The Reza Patent discloses the concept of a skin treatment which includes a mixture of a base which consists of liquid extract from a mixture of tomatoes and apples once a spontaneous chemical reaction is initiated by the mixture of the two crushed plants is completed. Specifically, the patent discloses: "A method for manufacturing a composition comprising crushing tomatoes and apples, mixing the crushed tomatoes and apples together in a weight ratio of tomatoes to apples between 0.8 and 1.25 to produce a mixture (M), allowing the mixture (M) to stand for about twenty-four hours, and filtering the mixture (M) after the standing for about twenty-four hours to produce a filtered liquid as the composition."

The Sobol Patent discloses manufacturing a skin treatment by a method of fermenting vegetable hydrolysate to create a therapeutically effective preparation. This includes various chemical combinations to treat scars, wrinkles and healing of burns. The patent discloses the following method:

"A method for producing a fermented hydrolyzed medium containing non-pathogenic microorganisms and products of their metabolism comprising the steps of:
  a) providing at least one solid food ingredient reduced to small pieces;
  b) providing at least one biocompatible liquid ingredient containing at least one non-pathogenic microorganism;
  c) mixing said solid food ingredient with said biocompatible liquid ingredient thereby obtaining a mixture in proportions of about 10-90% liquid to about 70-75% solid food by weight;
  d) adding a sugar by mixing the sugar into the mixture at about 0.1-30% by weight; and
  e) fermenting the mixture at 10-58 degrees C. until acidity reaches at least about 300 degrees Terner; whereby obtaining high acidity medium with high concentration of microorganisms and products of their metabolism."

The Boreyko Published Patent Application teaches the general concept of nutraceutical compositions including various fruits and vegetables for a variety of conditions including skin ailments.

The Mahalingam Published Patent Application discloses using various fruits and vegetables to improve the aesthetic appearance of the skin.

The McArthur Published Patent Application discloses a process for treating a fruit or a vegetable to arrive at a composition which is believed to help provide benefits to the skin. The process includes:

"A process for making a composition suitable for topical application comprising the steps of a) heating at least one fruit and/or vegetable pulp to up to a temperature in the range of about 40° C. to 100° C.; b) mixing between 1 and 40% w/w of a mild base with the heated fruit and/or vegetable pulp. There is also provided a fruit and/or vegetable derived composition suitable for topical application prepared by the above process. There is further provided a fruit and/or vegetable derived composition comprising at least one fruit and/or vegetable-derived pulp and a mild base, said composition having a pH in the range of about 7.5 to about 9.5."

The Barenholz Patent discloses treatment of skin ailments that have come from UV radiation and other types of harmful radiation. The concept is to encapsulate within liposomes substantially water-immiscible carotenoids.

The Mahalingam Patent discloses active extracts to lighten skin, lips, hair and/or nails. The extracts include *Butea frondosa, Naringi crenulata* and *Stenoloma chusana*. These three are added to additional extracts as set forth in Column 3 Line 54 which are *Azadirachata indica, Glycyrrhiza glabra linn., Morinda citrifolia*, tomato glycolipid, or any combinations thereof, can reduce melanin pigmentation of hair, skin, lips and/or nails.

The patent alleges:

"Lightening of hair, skin, lips and/or nails, as used in the present invention, means one or more of the following benefits is achieved. These benefits include bleaching hyper-pigmented hair, skin, lips, and/or nails; reducing age spots; evening or optimizing skin discoloration; improving the appearance of dark circles under the eyes; treating melasma, cholasma, freckles, after-burn scars, and post-injury hyperpigmentation; bleaching hair on the scalp, legs, face and other areas where bleaching and color reduction are desired; and bleaching nail stains."

The McArthur Published Patent Application has the following disclosure:

"Typically, a composition of the present invention is topically applied to an animal, preferably a human, for the treatment or prophylaxis of all epidermal disorders including psoriasis, eczema, insect bites, general epidermal irritation and redness including Rosaceae and itchiness, alopecia, circulatory disorders affecting the epidermis, sunburn, windsurf and first, second and third degree burns, healing of sores, wounds and skin infections, skin cancers including sunspots, skin melanomas, and also alleviates some gum diseases and mouth ulcers and other gum and mouth dermatological disorders. Also typically, the composition of the present invention can be topically applied to arthritic joints to alleviate pain and swelling associated with all forms of arthritis as well as general joint and muscle aches and pains. Also typically, the composition of the present invention is applied as a general pain reliever. It can also be typically applied to prevent sunburn."

The Bengmark Published Patent Application discloses a formulation which includes one antioxidant, vitamin, mineral, amino acid, peptide or protein and also includes various fruits and vegetables for use to treat burns of the skin. Specifically, the patent has the following claim:

"A method for manufacturing a formulation for the prevention or treatment of stress-induced inflammatory disorder comprising providing *Pediococcus pentosaceus* 16:1 (LMG P-20608), *Leuconostoc mesenteroides* 23-77:1 (LMG P-20607), *Lactobacillus paracasei* subsp *paracasei* F-19 (LMG P-17086), and *Lactobacillus plantarum* 2362 (LMG P-20606) wherein the bacterial strains are in an amount of at least $10^{11}$ CFU/ml of each of the bacteria and at least four different fibres."

The Giradiere European Patent Application discloses the treatment of irritated, blotchy and sunburned skin by using products including tomato juice. The patent application claims:

"A composition for making a coating on human tissue so as to apply thereto an active substance, the composition comprising the active substance, a first solution of a water-soluble alginate and a second solution of an appropriate metal salt which is capable of coagulating the alginate, such that when the solutions are separately applied to the tissue the alginate is coagulated to make the coating."

The Japanese Patent Application discloses a skin bleaching lotion which contains tomato juice as an active ingredient. The applications claims that the content of tomato extract is preferably 0.00005-5 wt % as a solid content.

While the above prior art has extensively discussed the general concept of utilizing a tomato or portions of a tomato or products derived from a tomato to help treat the skin, none of these formulations appear to have been effective and are primarily of a theoretical nature.

There is a significant need for an improved topical lotion and/or spray to help relieve the pain and heal burns on the skin of both humans, mammals and other animals which do not have some of the negative side effects of prior art compositions as discussed above.

SUMMARY OF THE INVENTION

The present invention is a topical treatment, which can be in the form of lotion, spray or other topically administered composition, which is used to enhance healing of burns, ultraviolet and radiation erythema. The treatment not only reduces pain and inflammation, prevents blistering, and maintains flexibility of the skin, but also accelerates the normal healing process.

The present invention is a concentrated tomato-derived topical formulation that significantly improves the healing time in first- and second-degree burns (thermal skin injury), in sunburn (ultraviolet skin injury) and radiation-induced erythema (ionizing radiation-induced skin injury).

It is an object of the present invention to create a formulation wherein the well-established photoprotective effects of systemically administered carotenoids may also be extended to topically delivered carotenoids and derivatives thereof.

The present invention includes a topical formulation that contains high levels of the active principles from tomatoes, such as lycopene and related carotenoids, certain phenolic acids, which have known anti-inflammatory properties, as well as other exogenously-added natural compounds.

Further novel features and other objects of the present invention will become apparent from the following detailed description and discussion.

DETAILED DESCRIPTION OF THE PREFERRED EMBODIMENTS

Although specific embodiments of the present invention will now be described, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention involves a topical composition and method of producing the same which is useful to treat minor burns caused by thermal, UV or radiation exposure. The present invention claims the composition which contains the following in a dermatologically acceptable cream, ointment or spray base:

1. A concentrated preparation obtained from tomatoes, which may be one of the following, or a combination thereof:
   a. A water-soluble powder obtained by concentration of mashed or crushed tomatoes under vacuum, followed by a drying process (1-20% by wt.). By way of example, the drying process can be selected from the group consisting of freeze drying, spray drying, or any other acceptable drying method known to those skilled in the art.
   b. An oleoresin (viscous liquid) extract prepared from tomatoes and/or tomato paste by solvent extraction. (1-20% by wt), or any other acceptable extraction method known to those skilled in the art.
2. Compounds naturally present in tomatoes, which may be obtained via isolation from the concentrated tomato preparation described above or from synthetic sources, to include at least one member, but not limited to one member, of the following groups:
   a. Carotenoids
      i. Lycopene (0.1-20%)
      ii. Beta-carotene (0.05-15%)
      iii. Phytoene (0.0001-2%)
      iv. Phytofluene (0.0001-2%)
   b. Phenolic Acids
      i. Caffeic acid (0.1-5%)
      ii. Quinic acid (0.1-5%)
      iii. Ferulic acid (0.1-5%)
      iv. Chlorogenic acid (0.1-5%)

3. Antioxidants to include at least one member, but not limited to one member, of the following:
   a. Ascorbyl palmitate (0.05-2%)
   b. Alpha-tocopherol or mixed tocopherols (0.1-5%)
   c. Retinyl palmitate, or compounds that are converted to Vitamin A in vivo (0.05-2%).
4. Anti-inflammatory botanicals
   a. *Calendula* extract (0.1-1%)—marigold extract (alcoholic tincture)
   b. *Arnica montana* (0.5-5%)—(alcoholic tincture or oil).
5. Antibacterials
   a. Tea tree oil (0.1-2.5%)
   b. Grapefruit seed extract (0.25-5%)—oil.

The present invention can be described as a concentrated preparation comprising: (a) a water-soluble powder obtained by concentration of mashed or crushed tomatoes under vacuum, followed by a drying process, (b) at least one carotenoid, (c) at least one phenolic acid, (d) at least one antioxidant, (e) at least one anti-inflammatory, and (f) at least one antibacterial. The at least one carotenoid is selected from the group consisting of (i) Lycopene (0.1-20%), (ii) Beta-carotene (0.05-15%), (iii) Phytoene (0.0001-2%), and (iv) phytofluene (0.0001-2%). The at least one phenolic acid is selected from the group consisting of (i) Caffeic acid (0.1-5%), (ii) Quinic acid (0.1-5%), (iii) Ferulic acid (0.1-5%), and (iv) Chlorogenic acid (0.1-5%). The at least one antioxidant is selected from the group consisting of (i) Ascorbyl palmitate (0.05-2%), (ii) Alpha-tocopherol or mixed tocopherols (0.1-5%), and (iii) Retinyl palmitate or retinol (0.05-2%), or any other related compounds that are converted to Vitamin A in vivo. The at least one anti-inflammatory botanical is selected from the group consisting of (i) *Calendula* extract (0.1-1%)—marigold extract (alcoholic tincture), and (ii) *Arnica montana* (0.5-5%)—(alcoholic tincture or oil). The antibacterial is selected from the group consisting of (i) Tea tree oil (0.1-2.5%) and (ii) Grapefruit seed extract (0.25-5%)—oil. This concentrated preparation is combined with a base to create a topical cream, ointment, or spay. One example of a cream base is a formulation comprising:
   a. Glycerine (1-20%);
   b. White petrolatum (3-30%);
   c. Glyceryl monostearate (1-5%);
   d Cetyl alcohol (1-5%);
   e. Stearyl alcohol (1-5%);
   f. Isopropyl myristate (1-10%);
   g. Shea Butter (1-25%);
   h. Allantoin (0.5-5%);
   i. Preservatives selected from the group consisting of sodium benzoate, which is present at a concentration of 1/10 of 1%, and EDTA; and
   j. Deionized water (20%-40% by volume).

Other dermatologically acceptable cream, ointment or spray bases may be employed as appropriate by those skilled in the art.

The present invention can also be described as a concentrated preparation comprising: (a) an oleoresin extract prepared from tomatoes and/or tomato paste by solvent extraction or any other extraction process, (b) at least one carotenoid, (c) at least one phenolic acid, (d) at least one antioxidant, (e) at least one anti-inflammatory, and (f) at least one antibacterial. The at least one carotenoid is selected from the group consisting of (i) Lycopene (0.1-20%), (ii) Beta-carotene (0.05-15%), (iii) Phytoene (0.0001-2%), and (iv). Phytofluene (0.0001-2%). The at least one phenolic acid is selected from the group consisting of (i) Caffeic acid (0.1-5%), (ii) Quinic acid (0.1-5%), (iii) Ferulic acid (0.1-5%), and (iv) Chlorogenic acid (0.1-5%). The at least one antioxidant is selected from the group consisting of (i) Ascorbyl palmitate (0.05-2%), (ii) Alpha-tocopherol or mixed tocopherols (0.1-5%), and (iii) Retinyl palmitate or retinol (0.05-2%) or other related compounds that are converted to Vitamin A in vivo. The at least one anti-inflammatory botanical is selected from the group consisting of (i) *Calendula* extract (0.1-1%)—marigold extract (alcoholic tincture), and (ii) *Arnica montana* (0.5-5%) (alcoholic tincture or oil). The antibacterial is selected from the group consisting of (i) Tea tree oil (0.1-2.5%) and (ii) Grapefruit seed extract (0.25-5%)—oil. This concentrated preparation is combined with a base to create a topical cream, ointment, or spay. An example of a cream base is formulation comprising:
 a. Glycerine (1-20%);
 b. White petrolatum (3-30%);
 c. Glyceryl monostearate (1-5%);
 d Cetyl alcohol (1-5%);
 e. Stearyl alcohol (1-5%);
 f. Isopropyl myristate (1-10%);
 g. Shea Butter (1-25%);
 h. Allantoin (0.5-5%);
 i. Preservatives selected from the group consisting of sodium benzoate, which is present at a concentration of ⅒ of 1%, and EDTA; and
 j. Deionized water (20%-40% by volume).

A method for producing a tomato oleoresin which is within the course and scope of the present invention is as follows: Fresh, ripe red tomatoes (washed, de-stemmed, cores removed, and thoroughly crushed) or tomato paste are heated to approximately 100° C. to facilitate evaporation of water; heat is then reduced to 75° C. and this temperature maintained for a period of about 30 minutes. Multiple extractions are then carried out using ethyl acetate/hexane or hexane/acetone/ethanol (50:25:25). Filtration and removal of solvent yields the oleoresin, which appears as a dark red oil.

An example of a suitable cosmetic cream base which is within the course and scope of the present invention is a composition comprising the following:
Glycerine (1-20%)
White petrolatum (3-30%)
Glyceryl monostearate (1-5%)
Cetyl alcohol (1-5%)
Stearyl alcohol (1-5%)
Isopropyl myristate (1-10%)
Shea Butter (1-25%)
Allantoin (0.5-5%)
Preservatives, q.s.—an example of a preservative is sodium benzoate, which is typically present at a concentration of ⅒ of 1%. EDTA is also a suitable preservative for these purposes.
Deionized water, q.s. (20%-40% by volume)

The formulation sequence for the topical preparation in a cream base (components as described above) is as follows:

Tomato powder is dissolved in deionized water. Glycerine is added, and the mixture is heated to at least 70° C., at which time the phenolic acids are added, stirring constantly until dissolved. Any preservatives such as EDTA or sodium benzoate may be added at this time, if desired. This aqueous-phase mixture is maintained at this temperature for 30 minutes. Separately, the components of the oil phase (glyceryl monostearate, stearyl alcohol, shea butter, petrolatum, cetyl alcohol, isopropyl myristate) are combined and heated until the solids melt (approximately 65° C.). The mixture is maintained at this temperature while the tomato oleoresin, carotenoids, vitamin antioxidants, anti-inflammatory botanical extracts, allantoin, and antibacterial oils (tea tree oil and grapefruit seed extract) are added. Any fragrance, if desired, may be added here. The oil phase is added carefully to the aqueous phase, stirring constantly. The mixture is then further emulsified using a homogenizer/mixer while simultaneously cooling it rapidly to below 40° C. to produce a cream suitable for topical application.

The method is described more broadly as a method of producing a topical preparation comprising:
 a. an aqueous phase including
  (i). tomato powder is dissolved in deionized water,
  (ii). Glycerine is added, and the mixture is heated to at least 70° C., at which time phenolic acids are added, stirring constantly until dissolved;
  (iii). adding preservatives such as EDTA or sodium benzoate, this aqueous-phase mixture is maintained at this temperature for approximately 30 minutes;
 b. an oil phase including separately, components of an oily phase which are glyceryl monostearate, stearyl alcohol, shea butter, petrolatum, cetyl alcohol, isopropyl myristate are combined and heated to approximately 65 degrees centigrade until the solids melt, the mixture is maintained at this temperature while a tomato oleoresin and at least one carotenoid are added;
 c. the oil phase is added carefully to the aqueous phase, stirring constantly; and
 d. the mixture is then further emulsified using a homogenizer/mixer while simultaneously cooling it rapidly to below 40° C. to produce a topical preparation.

After at least one carotenoid is added, then also adding at least one antioxidant, an anti-inflammatory, at least one botanical extract, allantoin, and at least one antibacterial oil. Also a fragrance may be added between steps "c" and "d".

The present invention describes a topical formulation containing high levels of the active principles of tomatoes, such as lycopene and related carotenoids, certain phenolic acids, which have known anti-inflammatory properties, as well as other exogenously-added natural compounds. It should have the equivalent or heightened beneficial effects as compared to those of fresh tomatoes without the impracticalities associated with using fresh fruit.

The present invention will yield higher efficacy due to fortification of the preparation with said exogenously added compounds as compared to tomatoes alone.

The inventors of the present invention have identified the active components from tomatoes and have obtained suitable extracts and concentrates of these ingredients for the preparation of formulations. The optimal concentrations of the several ingredients in the formulations for treatment of thermal burn injury may or may not be identical to those used in the treatment of ultraviolet injury and radiation induced injury.

For the present invention, formulations of tomato powder and/or extracts will be prepared in a cosmetically-pleasing vehicle with added antioxidants and other synergistic natural products, which possess known anti-inflammatory and antibacterial properties, emollients, dispersing agents, stabilizers, preservatives and other dermatologically compatible materials to prepare sterile topical ointment and spray formulations.

The ointment and/or cream formulations will provide a range of tomato powder/extract-derived active ingredients at various concentrations from 1-25%. The formulations will be packaged in appropriate containers such as tubes, jars, spray bottles and push pump bottles.

The topical spray formulations will provide a range of tomato powder/extract-derived 26 active ingredients at concentrations of 1-25%. The formulations will be packaged in appropriate containers.

The candidate formulations will be sterilized by steam or by radiation to achieve a sterility assurance of greater than $10^{-6}$ based on estimates of the bioburden.

The present invention is intended for the treatment of skin primarily in humans but also in other mammalian animals.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A concentrated preparation used as a topical treatment to improve healing time of first and second degree burns to human skin, the concentrated preparation consisting of the combination of:

a. a water-soluble powder obtained by concentration of mashed or crushed tomatoes under vacuum, followed by a drying process;

b. at least one carotenoid which contains 6-20% lycopene;

c. at least one phenolic acid which contains 0.1-5% caffeic acid;

d, at least one antioxidant which contains 0.1-5% alpha-tocopherol or mixed tocopherols;

e. at least one anti-inflammatory botanical which contains 0.1-1% alcoholic tincture of *Calendula* extract; and f. at least one antibacterial which contains 0.1-2.5% tea tree oil.

* * * * *